United States Patent [19]

Maruhnic

[11] 4,448,060
[45] May 15, 1984

[54] VISCOSITY MEASUREMENT USING PRESSURIZED VISCOMETER DEVICE

[75] Inventor: Peter Maruhnic, Pennington, N.J.

[73] Assignee: HRI, Inc., Gibbsboro, N.J.

[21] Appl. No.: 353,456

[22] Filed: Mar. 1, 1982

[51] Int. Cl.³ .......................................... G01N 11/12
[52] U.S. Cl. ...................................................... 73/57
[58] Field of Search ............................ 73/57; 422/119

[56] References Cited

U.S. PATENT DOCUMENTS 3,717,026  2/1973  Ito ............................................. 73/57

OTHER PUBLICATIONS

J. B. Irving et al., An Automated High Pressure Viscometer, J. Phys. E. (G.B.), vol. 4, No. 3, Mar. 1971, pp. 232–236.
L. H. Abbot et al., A System for Viscosity Measurements etc., A.S.L.E. Transactions, vol. 24, 1, 125–131, Jan. 1981.

Primary Examiner—S. Clement Swisher
Attorney, Agent, or Firm—Vincent A. Mallare

[57] ABSTRACT

A viscosity measuring method and viscometer device for remotely determining viscosity of fluids within an enclosed container. The viscometer device comprises a vertically-oriented tubular probe which contains a tube enclosed by multiple adjacent electromagnetic coils, and the tube contains a movable magnetizable core-float member. When measuring viscosity of a fluid, the movable core-float member is first magnetically lifted to the upper end of the tube by sequential energizing and de-energizing of the electromagnetic coils, then the core-float is allowed to fall freely through the fluid to the lower end of the tube. The fluid viscosity is determined by the elapsed time for the core-float to fall through the fluid. The viscosity measuring method and viscometer device is particularly useful inside a reactor containing fluid and operated at high pressure and temperature conditions.

5 Claims, 3 Drawing Figures

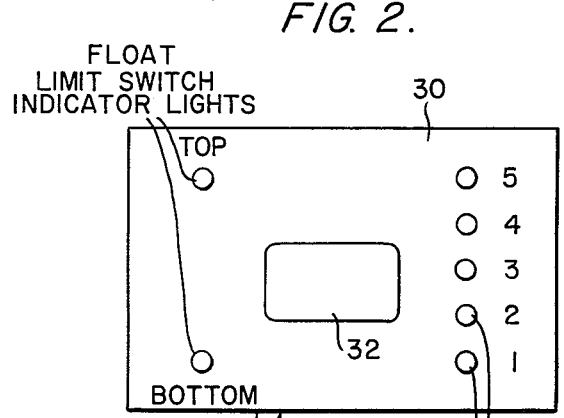
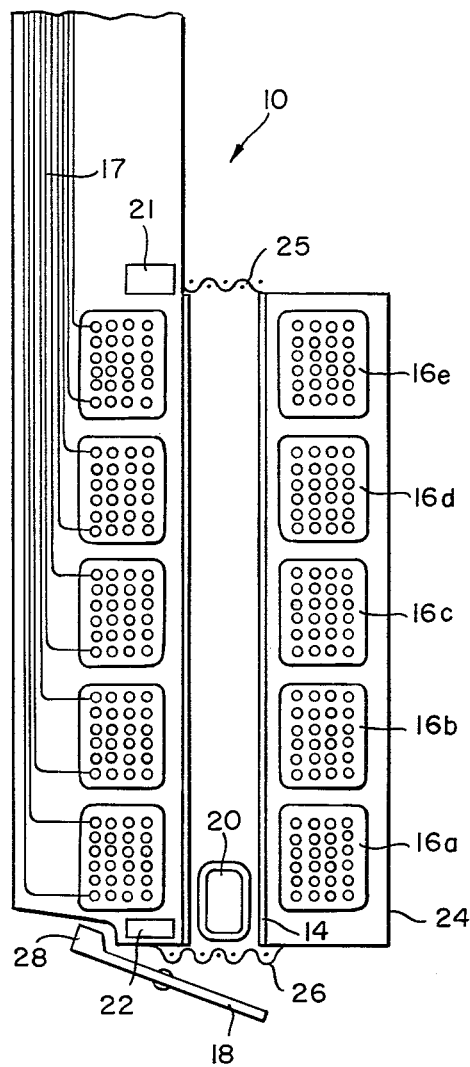
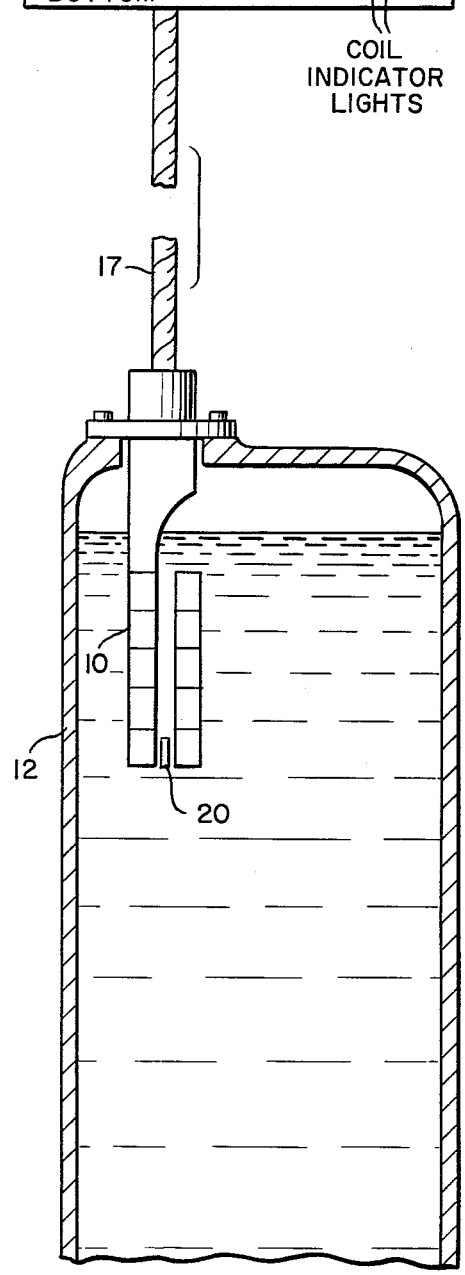
FIG. 1.
FIG. 2.

VISCOSITY MEASUREMENT USING PRESSURIZED VISCOMETER DEVICE

BACKGROUND OF INVENTION

This invention pertains to viscosity measurements for fluids and liquids under remote or pressurized conditions, and particularly to a viscometer device suitable for making on-line viscosity measurements of fluids inside a reactor vessel under high pressure and temperature conditions.

There is a great need in reaction processes, such as those using fluidized beds and ebullating beds of catalyst, to measure fluid or liquid viscosity inside reactors operating at high pressure and temperature conditions, such as 100–10,000 psig pressure and 100°–1,000° F. temperature. A major problem with previous attempts at directly measuring fluid viscosity in pressurized vessels under such conditions has been obtaining a suitably tight low friction seal between a conventional rotating shaft type viscometer and the wall of the high pressure vessel. The present invention eliminates use of such rotating shafts and seals by using the known principle of measuring fluid viscosity by means of a float member freely falling through the fluid, but accomplishing such action remotely within a pressurized reactor.

SUMMARY OF INVENTION

This invention provides a method and apparatus for remotely measuring viscosity of a fluid contained within a pressurizable enclosure. The viscometer apparatus comprises an elongated probe device having a non-magnetic tube surrounded by multiple electromagnetic coils located adjacently along the axis of the tube, and containing a movable magnetizable core-float member such as a cylinder containing iron. The probe device is rigidly mounted in the enclosure so as to be oriented substantially vertically and immersed in a fluid or liquid therein, the viscosity of which is to be measured periodically. In operation, the fluid is allowed to enter the tube, the moveable magnetizable core-flow member is lifted to the tube upper end by sequentially energizing and deenergizing the electromagnetic coils, and then the movable core-float member is allowed to fall through the fluid to the bottom of the tube. The elapsed time of fall for the magnetizable core-float member is measured by suitable electrical timing means, and the elapsed time is related to the viscosity of the fluid or liquid within the enclosure.

Although this invention can be used for measuring the viscosity of any remotely located fluid or liquid contained within an enclosure, it is particularly useful for measuring the viscosity of process fluids or liquids contained within pressurized reactor vessels operating at elevated pressure and temperature conditions, such as petroleum and coal-derived liquids.

BRIEF DESCRIPTION OF DRAWINGS

FIG. 1 is a cross-sectional elevation view of a viscosity measuring device arranged in accordance with the present invention.

FIG. 2 is a cross-sectional elevation view of a pressurizable vessel showing the viscosity measuring device installed in the vessel and connected schematically to electrical control circuits and timing means.

DESCRIPTION OF INVENTION

Figure 3:
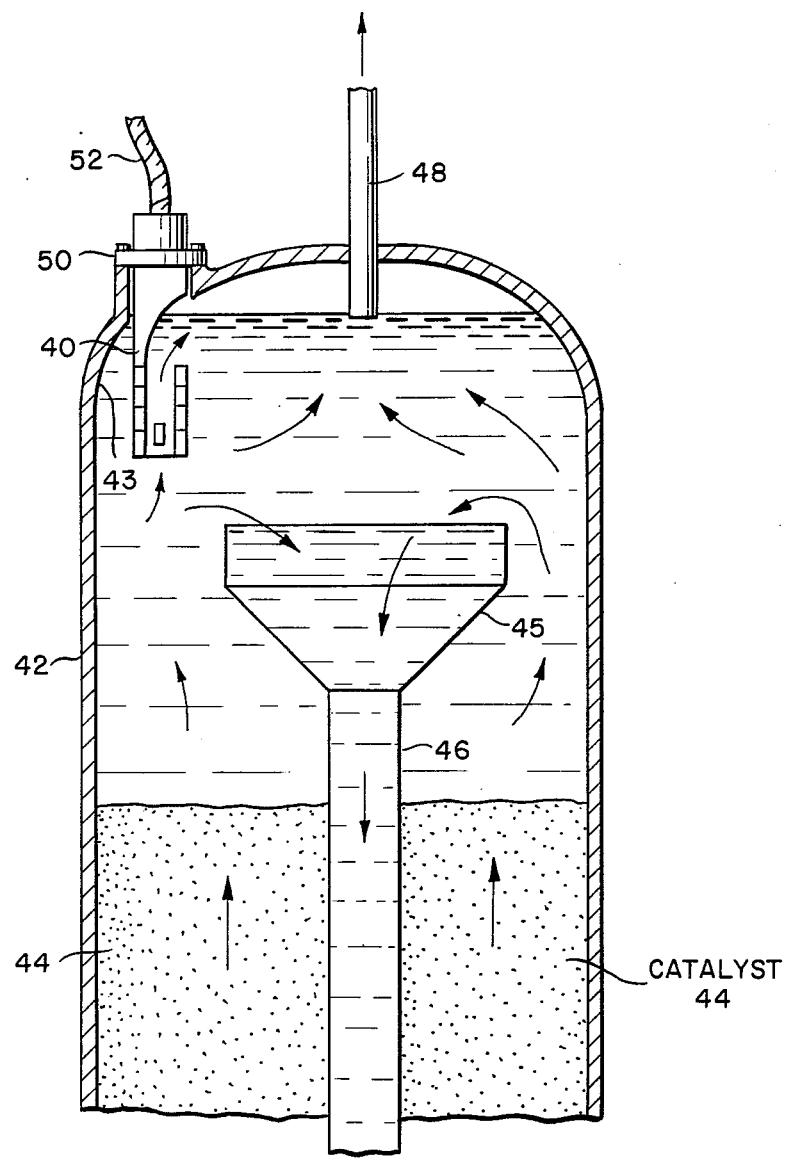
FIG. 3 is a cross-sectional elevation view of the upper portion of an ebullated catalyst bed reactor showing the viscosity measuring device installed in the reactor.

In the present invention the viscometer device is generally shown in FIG. 1, in which a removable tubular probe device 10 is provided and inserted vertically into a liquid contained within a pressurizable vessel 12. The probe device essentially comprises a tube 14 encircled by multiple adjacent electromagnetic coils 16 located along the tube axis, and the tube contains a movable magnetizable core-float member 20 containing sufficient iron to be readily magnetizable. Although at least three electromagnetic coils will usually be used in the viscometer device, more than about 10 coils are usually not practical or needed. Proximity switches 21 and 22 are located at the top and bottom ends of the tube 14 so as to indicate the position of the movable core-float member 20, which can be a wrought iron cylinder having length at least about 0.8 the height of each coil 16, and preferably having length between 0.9 and 1.5 the height of each coil. The electromagnetic coils 16, switches 21 and 22 and electrical conducting wire leads 17 are embedded and sealed in a suitable electrical insulating material 24, such as a plastic resin, glass wool, or refractory material depending upon the temperature of the liquid and are thus not exposed to the liquid. The tubular probe device 10 is at least about 6 inches long and need not exceed about 24 inches in length.

When the viscometer device is used in reactors containing solid particles, screens 25 and 26 are provided across the top and bottom ends respectively of the tube 14, to prevent such solids contained in the liquid, such as catalyst particles, from entering the tube 14. A baffle or suitable closure device 18, such as a movable plate or butterfly valve is provided at the bottom end of the tube 14 to permit flushing the tube with reactor liquid when the closure is open, and also to prevent liquid turbulence inside the tube when closed during a viscosity measurement. If desired to avoid corrosion or deposits on the magnetizable core-float 20, it can be encapsulated with a plastic or ceramic material 20a, depending on the liquid temperature. Also, the inside of the tube can be coated to minimize friction and also to minimize or prevent the liquid sticking to the surfaces.

The electrical wire leads 17 from the electromagnetic coils and switches are connected to a suitable control circuit (not shown) and to control panel 30. The panel 30 contains the necessary on/off switches for the multiple electromagnetic coils used to lift the core-float 20 and indicator lights for the upper and lower proximity switches, and an accurate timer means 32.

The operating sequence for the fluid viscosity measuring device is basically as follows:

With power on to the first or bottom electromagnetic coil 16a, the tube closure 18 is open and the tube is flushed with liquid by the natural upward flow of liquid in the reactor or vessel 12. Then, the second or next adjacent coil 16b from the bottom is energized and then the first coil 16a is deenergized. This sequential action causes the magnetizable core-float to move upward and be retained by the next upper coil 16b. This sequence is repeated until only the top coil is energized and the lower coils are all deenergized, and the core-float 20 is located at the upper end of the tube 14, thereby activating the upper limit switch 21. Meanwhile, deenergizing the first or lowest coil 16a has caused the bottom plate closure device 18 to close by action of a counter-weight 28. This prevents the flow of reactor liquid inside the viscometer tube 14 and prevents turbulence therein during liquid viscosity measurements.

When it is desired to take a measurement of liquid viscosity within the reactor, the top electromagnetic coil is deenergized, thus allowing the core-float 20 to fall freely and simultaneously open the top limit switch 21. At the instant the top switch is opened, the timer 32 is started. After the core-float 20 falls to the bottom of the tube, the bottom limit switch 22 is closed and the timer is stopped. The elapsed time for the core-float member to fall from the top to the bottom of the tube is related to the viscosity of the fluid or liquid within the vessel or reactor at the particular time. The viscometer tube and movable core-float combination is calibrated for elapsed time versus fluid viscosity prior to installation of the device in the vessel.

For manual operation of the viscometer device, energizing the electromagnetic coils 16 in succession to lift the core-float 20 to the upper end of the tube 14 can be accomplished by simply closing and opening switches to energize and deenergize the coils in sequence from bottom to top coil surrounding the tube. The timer 32 can be started with a switch when the top limit switch indicator light goes out, and stopped when the bottom limit switch indicator light goes on. For automatic operation, the sequence of opening and closing switches for the electromagnetic coils and timer can be programmed by means of a cycle timer or microprocessor (not shown).

This viscometer device is particularly useful for installing inside a reactor operated at elevated pressure and temperature conditions, such as 100–10,000 psig pressure and 100°–1000° F. temperature. It is particularly useful for installing in the upper portion of a reactor containing an ebullated catalyst bed for coal liquefaction and hydrogenation at process conditions of 700°–950° F. temperature and 1000–5000 psig pressure to measure the viscosity of the coal-derived liquid slurry containing some vapor, unconverted coal and ash solids. As generally shown by FIG. 3, pressurized viscometer 40 is installed in the upper portion of reactor 42 containing ebullated bed 44 of particulate catalyst. The bed 44 is expanded about 10–52% above its settled height by upflow of liquid and gas through the bed. The liquid and gas are separated by gas-liquid separation device 45 above bed 44, and the liquid is recycled downwardly through conduit 46 by a pump (not shown). Viscometer 40 is removably installed in the liquid in a substantially vertical position in reactor 42 near the wall 43 and at a level above gas-liquid separation device 45 and below the lower end of liquid withdrawal conduit 48. Viscometer device 40 is removably attached to reactor 42 by bolted flange 50. The viscosity measurement is substantially the same as described by FIG. 2.

This invention will be further described by reference to the following examples, which should not be construed as limiting in scope.

EXAMPLE 1

To demonstrate the feasibility of lifting a magnetizable core-float member within a vertical tube by electromagnetic coil means operated in sequence, the following experiments were conducted:

A glass tube 0.4 inch inside diameter×8 inch long was held in a vertical position with four adjacent electromagnetic coils positioned to encircle the tube, each coil being 1.5 inches outside diameter×1.25 inches long. The coils were held in position to maintain a 0.38 inch vertical gap between coils, and the overall length of the portion of glass tube surrounded by the coils was 6.25 inches. A wrought iron cylinder 0.38 inch diameter×2 inches long was placed in the bottom of the tube with 0.5 inch of the upper end of the cylinder intruding upward into the No. 1 bottommost coil. The No. 1 coil and the No. 2 coil located directly above were energized and the cylinder was lifted upward in the tube so that 0.5 inches of the cylinder upper end extended into the No. 2 coil. No. 1 coil was then deenergized and No. 3 coil located above No. 2 coil was energized; the cylinder moved upward to the No. 3 higher coil. No. 4 coil was energized and No. 2 coil was then energized; the cylinder moved upward to the No. 4 coil. No. 3 coil was then deenergized, and the cylinder remained in its' uppermost travel position in the tube, being magnetically supported by No. 4 coil about 6.5 inches from the bottom starting position. Then upon deenergizing No. 4 (uppermost) coil, the cylinder fell freely through the glass tube to the initial bottom starting position.

This experiment demonstrated the validity of using adjacent electromagnetic coils sequentially energized and deenergized to lift a magnetizable core-float member to the upper end of a non-magnetic tube, then dropping the core-float through a fluid such as a liquid to measure the viscosity of the fluid.

A second experiment used a wrought iron cylinder 0.25 inch diameter×1.5 inch long, and the four electromagnetic coils were stacked vertically with 0.38 inch gaps between coils. The cylinder was lifted to the top end of the tube as before by energizing each upper coil and then deenergizing the lower coils in sequence.

A third experiment was performed using the same glass tube and electromagnetic coils, except the coils were repositioned vertically around the tube so as to touch each other. A shorter wrought iron cylinder, 1.125 inches long×0.38 inch diameter, was placed in the bottom of the tube with 0.5 inch of the cylinder intruding upward into the No. 1 coil. By energizing each upper coil and then deenergizing the lower coils in sequence as in the prior experiments, the cylinder was magnetically lifted to the top of the adjacent stacked electromagnetic coils. Then by deenergizing the top coil the cylinder was allowed to fall freely to the bottom of the tube. In a fourth experiment, a cylinder 0.625 inch long could not be magnetically lifted in the tube by energizing and deenergizing the electromagnetic coils in sequence. It is thus noted that by positioning the electromagnetic coils with adjacent coils touching each other, a cylinder having length about 0.125 inch shorter than the coil could be magnetically lifted in the tube.

In a fifth experiment, the magnetizable cylinder was positioned to intrude about 0.5 inch into the No. 1 (lowest) electromagnetic coil, and all four electromagnetic coils were energized. The coils were then deenergized in sequence commencing with the lowest coil, and the cylinder was lifted sequentially upward and supported by the uppermost coil.

By these experiments, it was demonstrated that a magnetizable wrought iron cylinder having dimensions ranging from about 0.25 inch to 0.38 inch diameter and 1.125 inch to 2 inch long could be lifted within a 0.40 inch diameter glass tube by means of sequentially energizing each upper electromagnetic coil and deenergizing each lower electromagnetic coil placed around the tube, after which the cylinder was released to fall freely to the bottom starting position in the tube. These experiments simulated operations of the viscometer device to remotely measure viscosity of a fluid or liquid within an enclosed vessel.

EXAMPLE 2

The experiments of Example 1 were repeated using a non-magnetic austentic type stainless steel tube having 0.4 inch inside diameter and 0.44 inch outside diameter instead of the glass tube. The electromagnetic coil operation sequence used for lifting the wrought iron movable core-float member was the same as for Example 1. The magnetizable wrought iron cylinder was magnetically lifted to the upper end of the stainless steel tube and dropped as for Example 1, showing that a non-magnetic metal tube can be substituted for the glass tube.

Although this invention has been described broadly and with reference to certain embodiments thereof, it will be understood that modifications and variations to the device and its method of use can be made within the spirit and scope of the invention, which is defined by the following claims.

I claim:

1. A fluid viscosity measuring device which is installed in the upper portion of a pressurized reactor containing an ebullated catalyst bed and has its lower end located above the catalyst bed, said device comprising:
    (a) a vertically oriented non-magnetic tube containing a movable core-float member which is cylindrical shaped and contains sufficient iron to be magnetizable and has a diameter slightly smaller than the tube inner diameter;
    (b) multiple electromagnetic coils surrounding said tube, and enclosed within electrical insulating material which comprises a resin compound, said tube being surrounded by at least three adjacent electromagnetic coils each centrally located around the tube;
    (c) switching means for energizing and deenergizing said electromagnetic coils in a sequence so as to magnetically lift the magnetizable core-float member to the upper end of said tube and then release said member, said core-float member having a length of at least about 0.8 the height of each electromagnetic coil and the distance for movement of the core-float member is between about 6 and 24 inches; and
    (d) timing means for measuring the elapsed time for the core-float member to fall through said tube from the top to the bottom end of said tube.

2. A method for measuring viscosity of a fluid contained within a pressurizable enclosure, comprising:
    (a) inserting into an enclosure pressurized to 10–10,000 psig and containing a fluid having a temperature of 100°–1000° F., a tubular probe device comprising a non-magnetic tube surrounded by multiple adjacent electromagnetic coils, said tube containing a magnetizable movable core-float member which is lifted to the upper end of said tube by energizing the electromagnetic coil immediately above said core-float member, then deenergizing the electromagnetic coil immediately below said core-float member, thereby magnetically lifting the moveable magnetizable core-float member within said tube, and the upper and lower positions of said moveable core-float member being indicated by electrical switches located at each end of the tube;
    (b) allowing the fluid to enter said tube which is flushed by upflowing said fluid prior to magnetically lifting the core-float member to the upper end of said tube;
    (c) energizing and deenergizing said electromagnetic coils in sequence and magnetically lifting said moveable core-float member to the upper end of said tube and magnetically supporting said moveable core-float member by the uppermost electromagnetic coil;
    (d) deenergizing said uppermost electromagnetic coil and allowing the core-float member to fall through the fluid to the lower end of the tube; and
    (e) measuring the elapsed time for the moveable core-float member to fall through the fluid to the lower end of said tube, said time being from about 1 to about 10 seconds.

3. The method of claim 2, wherein the fluid in said tube is isolated by movable closure means before allowing the movable core-float member to fall through the fluid in the tube.

4. The method of claim 2, wherein said tubular probe device is removably inserted into a pressurizable reactor containing a bed of catalyst and the fluid therein is a hydrocarbon liquid and vapor mixture.

5. The method of claim 4, wherein the fluid is coal-derived liquid containing less than about 20 volume percent vapor.

* * * * *